United States Patent [19]

Hubele et al.

[11] Patent Number: 4,694,009

[45] Date of Patent: Sep. 15, 1987

[54] PESTICIDAL COMPOSITIONS

[75] Inventors: Adolf Hubele, Magden; Helmut Zondler, Bottmingen; Peter Riebli, Buckten, all of Switzerland; Wolfgang Eckhardt, Lörrach, Fed. Rep. of Germany

[73] Assignee: Ciba-Geigy Corporation, Ardsley, N.Y.

[21] Appl. No.: 746,432

[22] Filed: Jun. 19, 1985

[30] Foreign Application Priority Data

Jun. 25, 1984 [CH] Switzerland .......................... 3055/84

[51] Int. Cl.[4] .................. C07D 239/42; C07D 239/47; A61K 31/505
[52] U.S. Cl. .................................... 514/269; 514/275; 544/321; 544/332
[58] Field of Search ................. 544/321, 332; 514/269, 514/275

[56] References Cited

U.S. PATENT DOCUMENTS 3,906,098 9/1975 Barlow et al. ...................... 424/251

FOREIGN PATENT DOCUMENTS 135472 1/1985 European Pat. Off. ............ 544/332
56-65804 6/1981 Japan .

Primary Examiner—Robert Gerstl
Attorney, Agent, or Firm—Meredith C. Findlay; Kevin T. Mansfield

[57] ABSTRACT

The invention discloses novel N-(2-nitrophenyl)-2-aminopyrimidine derivatives of the general formula I

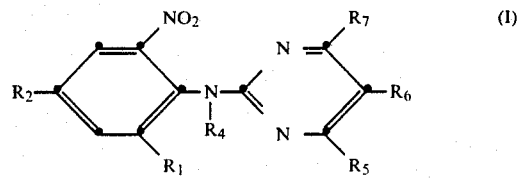

wherein
$R_1$ and $R_2$ are hydrogen, $NO_2$ or $CF_3$, with the proviso that only $R_1$ or $R_2$ can be $NO_2$;
$R_4$ is hydrogen or the —C(O)R' group, in which R' is $C_1$–$C_4$alkyl which is unsubstituted or substituted by halogen, $C_1$–$C_3$alkoxy or $C_1$–$C_3$alkylthio;
$R_5$, $R_6$ and $R_7$ are each independently halogen, nitro, cyano, thiocyano, $C_1$–$C_{12}$alkyl, $C_3$–$C_8$cycloalkyl, $C_1$–$C_8$alkylthio, $C_1$–$C_6$alkylsulfonyl, $C_1$–$C_6$alkylsulfoxyl, $C_3$–$C_6$alkenyl, $C_3$–$C_6$haloalkenyl, $C_3$–$C_6$alkynyl, $C_3$–$C_6$haloalkynyl, $C_3$–$C_6$alkenyloxy, $C_3$–$C_6$haloalkenyloxy, $C_3$–$C_6$alkenylthio, $C_3$–$C_6$alkynyloxy, $C_3$–$C_6$haloalkynyloxy, $C_1$–$C_8$alkyl which is substituted by halogen, cyano and/or $C_1$–$C_4$alkoxy, or are unsubstituted $C_1$–$C_8$alkoxy or halogen-substituted $C_1$–$C_8$alkoxy, the alkyl moiety of which may be interrupted by one or more single oxygen atoms, or are the Q—$(E)_n$—$(X)_m$ group, in which n is 0 or 1, m is 0 or 1, Q is phenyl which is unsubstituted or substituted by halogen, nitro, $C_1$–$C_3$alkyl, $CF_3$ and/or $C_1$–$C_3$alkoxy, or is a saturated or unsaturated heterocyclic radical containing one or more hetero atoms, E is a $C_1$–$C_3$alkylene bridge, and X is oxygen or sulfur, and $R_6$ and/or one of the radicals $R_5$ or $R_7$ can also be hydrogen.

Also disclosed are methods of preparing these compounds, and agrochemical compositions which contain one such compound as active ingredient. The invention further relates to the use of the novel compounds, or compositions containing them, in agriculture and related fields.

3 Claims, No Drawings

PESTICIDAL COMPOSITIONS

The present invention relates to novel N-(2-nitrophenyl)-2-aminopyrimidine derivatives of formula I below.

The invention further relates to the preparation of these compounds and to agrochemical compositions which contain at least one of these compounds as active ingredient. The invention also relates to the preparation of such compositions and to the use of the novel compounds or compositions for controlling harmful microorganisms, preferably phytopathogenic fungi and bacteria.

Specifically, the present invention relates to compounds of the general formula I

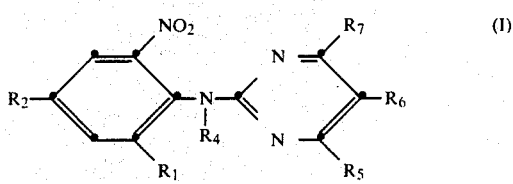

wherein
$R_1$ and $R_2$ are hydrogen, $NO_2$ or $CF_3$, with the proviso that only $R_1$ or $R_2$ can be $NO_2$;
$R_4$ is hydrogen or the —C(O)R' group, in which R' is $C_1$-$C_4$alkyl which is unsubstituted or substituted by halogen, $C_1$-$C_3$alkoxy or $C_1$-$C_3$alkylthio;
$R_5$, $R_6$ and $R_7$ are each independently halogen, nitro, cyano, thiocyano, $C_1$-$C_{12}$alkyl, $C_3$-$C_8$cycloalkyl, $C_1$-$C_8$alkylthio, $C_1$-$C_6$alkylsulfonyl, $C_1$-$C_6$alkylsulfoxyl, $C_3$-$C_6$alkenyl, $C_3$-$C_6$haloalkenyl, $C_3$-$C_6$alkynyl, $C_3$-$C_6$haloalkynyl, $C_3$-$C_6$alkenyloxy, $C_3$-$C_6$haloalkenyloxy, $C_3$-$C_6$alkenylthio, $C_3$-$C_6$alkynyloxy, $C_3$-$C_6$haloalkynyloxy, $C_1$-$C_8$alkyl which is substituted by halogen, cyano and/or $C_1$-$C_4$alkoxy, or are unsubstituted $C_1$-$C_8$alkoxy or halogen-substituted $C_1$-$C_8$alkoxy, the alkyl moiety of which may be interrupted by one or more single oxygen atoms, or are the Q—$(E)_n$—$(X)_m$ group, in which n is 0 or 1, m is 0 or 1, Q is phenyl which is unsubstituted or substituted by halogen, nitro, $C_1$-$C_3$alkyl, $CF_3$ and/or $C_1$-$C_3$alkoxy, or is a saturated or unsaturated heterocyclic radical containing one or more hetero atoms, E is a $C_1$-$C_3$alkylene bridge, and X is oxygen or sulfur, and $R_6$ and/or one of the radicals $R_5$ or $R_7$ can also be hydrogen.

Depending on the number of indicated carbon atoms, alkyl by itself or as moiety of another substituent, e.g. alkoxy, haloalkyl, haloalkoxy etc., denotes for example the following straight chain or branched groups: methyl, ethyl, propyl, butyl, pentyl, hexyl, heptyl, octyl, nonyl, decyl, undecyl, dodecyl etc. and the isomers thereof, e.g. isopropyl, isobutyl, tert-butyl, isopentyl etc. Throughout this specification, a substituent prefixed by "halo" indicates that said substituent may be mono- to perhalogenated. Halogen and halo signify fluorine, chlorine, bromine or iodine. Hence haloalkyl is a mono- to perhalogenated alkyl radical, e.g. $CHCl_2$, $CH_2F$, $CCl_3$, $CH_2Cl$, $CHF_2$, $CH_2CH_2Br$, $C_2Cl_5$, $CH_2Br$, $CHBrCl$ etc., and is peferably $CF_3$. Alkenyl is for example 1-propenyl, allyl, 1-butenyl, 2-butenyl or 3-butenyl, and chains containing several double bonds. Depending on the number of indicated carbon atoms, cycloalkyl is for example cyclopropyl, cyclobutyl, cyclopentyl, cyclohexyl, cycloheptyl, cyclooctyl etc. Alkynyl is for example 2-propynyl, propargyl, 1-butynyl, 2-butynyl etc., with propargyl being preferred.

Throughout this specification, a saturated or unsaturated heterocyclic radical containing one or more hetero atoms will be understood as meaning a saturated or unsaturated 5- or 6-membered heterocyclic ring system containing 1 to 3 identical or different hetero atoms, e.g. oxygen, nitrogen or sulfur atoms. Typical representatives of such heterocyclic ring systems are: tetrahydrofuran, furan, tetrahydrothiophene, thiophene, pyrrolidine, pyrrole, pyrroline, pyrazole, imidazole, pyrazoline, oxazole, thiazole, isoxazole, isothiazole, pyran, dihydropyran, tetrahydropyran, thiopyran, dihydrothiopyran, tetrahydrothiopyran, pyridazine, dihydropyridazine, tetrahydropyridazine, pyrimidine, dihydropyrimidine, tetrahydropyrimidine, pyrazine, dihydropyrazine, tetrahydropyrazine, morpholine, thiazine, dihydrothiazine, tetrahydrothiazine, piperazine and triazine. $C_1$-$C_3$Alkylene is for example the following groups: —$CH_2$—, —$CH_2CH_2$—, —$CH_2CH_2CH_2$—, —$CH(CH_3)$—$CH_2$—, —$CH_2CH(CH_3)$—, —$CH(C_2H_5)$—, —$C(CH_3)_2$—. Alkylsulfoxyl is the alkyl-S(O)-group. Phenyl is $C_6H_5$.

At room temperature the compounds of formula I are oils, resins or mainly crystalline solids which have extremely valuable biocidal properties. They can be used for example in agriculture or related fields preventively and curatively for controlling phytopathogenic pests, e.g. fungi or bacteria. The compounds of formula I have an excellent biocidal activity and a broad activity spectrum when applied in wide ranges of concentration and their use poses no problems.

The following groups of compounds are preferred on account of their pronounced biocidal, especially phytofungicidal, properties:

Group Ia: Compounds of formula I, wherein $R_1$, $R_2$ and $R_4$ are as defined for formula I and $R_5$, $R_6$ and $R_7$ are each independently halogen, nitro, cyano, $C_1$-$C_6$alkyl, cyclopentyl, cyclohexyl, $C_1$-$C_3$alkylthio, $C_1$-$C_3$alkylsulfonyl, $C_1$-$C_3$alkylsulfoxyl, $C_3$-$C_4$alkenyl, propargyl, $C_1$-$C_3$alkyl which is substituted by halogen, cyano and/or $C_1$-$C_3$alkoxy, or are $C_1$-$C_6$alkoxy, the alkyl moiety of which is interrupted by 1 or 2 single oxygen atoms, or are the Q—$(E)_n$—$(X)_m$ group, in which n is 0 or 1, m is 0 or 1, Q is phenyl which is unsubstituted or substituted by halogen, nitro, methyl, $CF_3$ or methoxy, or is a pyridyl group, E is a methylene bridge, and X is oxygen or sulfur, and $R_6$ and/or one of the radicals $R_5$ or $R_7$ can also be hydrogen.

Group Ib: Compounds of formula I, wherein $R_2$ and $R_3$ are as defined for formula I, $R_4$ is hydrogen and $R_5$, $R_6$ and $R_7$ are each independently halogen, nitro, cyano, $C_1$-$C_6$alkyl, cyclopentyl, cyclohexyl, $C_1$-$C_3$alkylthio, $C_1$-$C_3$alkylsulfonyl, $C_1$-$C_3$alkoxysulfoxyl, $C_3$-$C_4$alkenyl, propargyl, $C_1$-$C_3$alkyl which is substituted by halogen, cyano and/or $C_1$-$C_3$alkoxy, or are $C_1$-$C_6$alkoxy, the alkyl moiety of which is interrupted by 1 or 2 single oxygen atoms, or are the Q—$(E)_n$—$(X)_m$ group, in which n is 0 or 1, m is 0 or 1, Q is phenyl which is unsubstituted or substituted by halogen, nitro, methyl, $CF_3$ or methoxy, or is a pyridyl group, E is a methylene bridge, and X is oxygen or sulfur, and $R_6$ and/or one of the radicals $R_5$ or $R_7$ can also be hydrogen.

Group Ic: Compounds of formula I, wherein $R_1$ is $CF_3$; $R_2$ is $NO_2$; $R_4$ is hydrogen, $R_6$ is hydrogen and $R_5$ and $R_7$ are each independently fluorine, chlorine, bromine, $C_1$-$C_3$alkyl, $C_1$-$C_3$haloalkyl, $C_1$-$C_3$alkoxy, $C_1$–$C_3$haloalkoxy, unsubstituted phenoxy or halogen-substituted phenoxy, $OCH_2OCH_3$, $OC_2H_4OCH_3$, $OCH_2OC_2H_5$, $OC_2H_4OC_2H_5$, $OC_2H_4OC_2H_4OC_2H_5$ or —S—(2-pyridyl).

Further, the following compounds of formula I, which are distinguished by special substitution characteristics, have particularly advantageous fungicidal properties:

Group IIa: Compounds of formula I, wherein $R_1$ is $CF_3$ and $R_2$ is $NO_2$, $R_4$ is hydrogen and $R_5$, $R_6$ and $R_7$ are as defined for formula I, with the exception of hydrogen.

Group IIb: Compounds of formula I, wherein $R_1$ is $CF_3$ and $R_2$ is $NO_2$, $R_4$ is hydrogen and $R_5$, $R_6$ and $R_7$ are halogen, $C_1$–$C_6$alkyl, $C_1$–$C_4$alkoxy, $C_1$–$C_3$alkylthio, $C_3$–$C_6$alkenyl, $C_3$–$C_6$haloalkenyl, $C_3$–$C_6$alkynyl, $C_3$–$C_6$haloalkynyl, $C_3$–$C_6$alkenyloxy, $C_3$–$C_6$alkynyloxy, $C_1$–$C_6$alkyl which is substituted by halogen or $C_1$–$C_4$alkoxy, or are alkoxy which is substituted by halogen or $C_1$–$C_4$alkoxy.

Examples of particularly preferred individual compounds are:

N-(2'-trifluoromethyl-4',6'-dinitrophenyl)-2-amino-4-chloro-6-difluoromethoxypyrimidine (1.1);

N-(2'-trifluoromethyl-4',6'-dinitrophenyl)-2-amino-4,6-dichloropyrimidine (1.2);

N-(2'-trifluoromethyl-4',6'-dinitrophenyl)-2-amino-4,5,6-trichloropyrimidine (1.69);

N-(2'-trifluoromethyl-4',6'-dinitrophenyl)-2-amino-4,5-dichloro-6-methoxypyrimidine (1.136);

N-(2'-trifluoromethyl-4',6'-dinitrophenyl)-2-amino-4-chloro-5-bromo-6-propin-2-yloxypyrimidine (1.133);

N-(2'-trifluoromethyl-4',6'-dinitrophenyl)-2-amino-4-chloro-5-bromo-6-propen-2-yloxypyrimidine (1.131);

N-(2'-trifluoromethyl-4',6'-dinitrophenyl)-2-amino-4,5-dichloro-6-(2,2,2-trifluoroethoxypyrimidine (1.143).

In accordance with the present invention, the compounds of formula I are prepared by reacting a compound of formula II

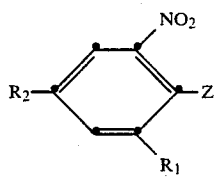
(II)

with a pyrimidine derivative of formula III

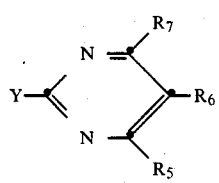
(III)

in the presence of a base, to give a compound of formula I'

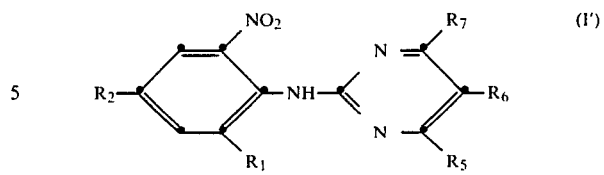
(I')

and to obtain an N-acylated derivative, N-acylating the compound of formula I' with a reactive derivative of the carboxylic acid of formula IV

$R_4COOH$ (IV)

in which formulae above the substituents $R_1$ to $R_7$ are as defined for formula I and Z and Y are $NH_2$ or halogen, with the proviso that, if Z is halogen, Y is $NH_2$ and, if Z is $NH_2$, Y is halogen.

The following reaction conditions are advantageous for the preparation of compounds of formula I and/or I':

The N-arylation of (II) with (III) to give (I') and the N-acylation of (I') with (IV) to give (I) take place with dehydrohalogenation. The reaction temperature of the N-arylation is in the range from $-20°$ to $+150°$ C., preferably from $-20°$ to $+30°$ C., and that for the N-acylation is in the range from $0°$ to $+180°$ C., preferably from $0°$ to $+150°$ C. or at the boiling point of the solvent or solvent mixture. In both reactions it is convenient to use an acid acceptor or a condensing agent. Examples of suitable acid acceptors or condensing agents are organic and inorganic bases, e.g. tertiary amines such as trialkylamines (trimethylamine, triethylamine, tripropylamine etc.), pyridine and pyridine bases (4-dimethylaminopyridine, 4-pyrrolidylaminopyridine etc.), alcoholates such as potassium tert-butylate, oxides, hyroxides, carbonates and bicarbonates of alkali metals and alkaline earth metals, as well as alkali metal acetates.

Hydrogen halide evolved can in some cases be removed from the reaction mixture by introducing an inert gas, e.g. nitrogen.

The reactions may be conducted in the presence of inert solvents or diluents. Examples of suitable solvents and diluents are: aliphatic and aromatic hydrocarbons such as benzene, toluene, xylenes, petroleum ether; halogenated hydrocarbons such as chlorobenzene, methylene chloride, ethylene chloride, chloroform, carbon tetrachloride, tetrachloroethylene; ethers and ethereal compounds such as dialkyl ethers (diethyl ether, diisopropyl ether, tert-butylmethyl ether etc.), anisole, dioxane, tetrahydrofuran; nitriles such as acetonitrile and propionitrile; N,N-dialkylated amides such as dimethylformamide; dimethyl sulfoxide; ketones such as acetone, diethyl ketone, methyl ethyl ketone; and mixtures of such solvents. In some cases the acylating or arylating agent itself may be used as solvent.

The reaction of (II) with (III) can also be carried out in an aqueous two-phase system in accordance with the generally known principle of phase transfer catalysis.

The following solvents for example are suitable for the organic water-immiscible phase: aliphatic and aromatic hydrocarbons such as pentane, hexane, cyclohexane, petroleum ether, ligroin, benzene, toluene, xylenes etc.; halogenated hydrocarbons such as dichloromethane, chloroform, carbon tetrachloride, ethylene dichloride, 1,2-dichloroethane, tetrachloroethylene etc.; or aliphatic ethers such as diethyl ether, diisopropyl ether, tert-butylmethyl ether etc. Examples of suitable phases transfer catalysts are: tetraalkylammonium halides, hydrogen sulfates or hydroxides, e.g. tetrabutylammonium chloride, tetrabutylammonium bromide, tetrabutylammonium iodide, triethylbenzylammonium chloride or triethylbenzylammonium bromide, tetrapropylammonium chloride, tetrapropylammonium bromide or tetrapropylammonium iodide etc. Suitable phase transfer catalysts are also phosphonium salts. The reaction temperatures are generally in the range from −30° to 130° C. or may also be at the boiling point of the solvent or mixture of solvents.

Unless otherwise expressly specified, one or more inert solvents or diluents may be present in the preparation of all starting materials, intermediates and final products mentioned herein. Examples of suitable inert solvents or diluents are: aliphatic and aromatic hydrocarbons such as benzene, toluene, xylenes, petroleum ether; halogenated hydrocarbons such as chlorobenzene, methylene chloride, ethylene chloride, chloroform, carbon tetrachloride, tetrachloroethylene; ethers and ethereal compounds such as dialkyl ethers (diethyl ether, diisopropyl ether, tert-butylmethyl ether etc.), anisole, dioxane, tetrahydrofuran; nitriles such as acetonitrile, propionitrile; N,N-dialkylated amides such as dimethylformamide; dimethyl sulfoxide; ketones such as acetone, diethyl ketone, methyl ethyl ketone; and mixtures of such solvents with each other. It can in some cases be convenient to carry out the reaction, or partial steps of a reaction, under an inert gas atmosphere and/or in absolute solvents. Suitable inert gases are nitrogen, helium, argon or, in certain cases, also carbon dioxide.

The above described preparatory process, including all partial steps, constitutes an important object of the present invention.

Phenyl-2-aminopyrimidine derivatives are already known as pesticidally and fungicidally effective compounds. However, they can not always fully meet the demands made of them in practice. Such compounds are described for example in Japanese published patent application No. 141 647. They are of the general formula

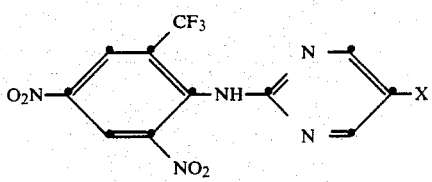

wherein X is hydrogen or halogen. In comparison, the compounds of the present invention are distinctly superior in their fungicidal activity to these known compounds.

Surprisingly, it has been found that the compounds of formula I have for practical purposes a very useful biocidal spectrum against fungi and bacteria, especially against phytopathogenic fungi and bacteria. They have very advantageous curative, systemic and, in particular, preventive properties, and can be used for protecting numerous cultivated plants. With the compounds of formula I it is possible to inhibit or destroy the pests which occur in plants or parts of plants (fruit, blossoms, leaves, stems, tubers, roots) in different crops of useful plants, while at the same time the parts of plants which grow later are also protected from attack by such phytopathogenic microorganisms and insects. Plant-destructive Acarina and Nematoda as well as undesired species of plants can also be successfully controlled with compounds of formula I.

As microbicides, the compounds of formula I are effective against the phytopathogenic fungi belonging to the following classes: Fungi imperfecti (e.g. Botrytis, Helminthosporium, Fusarium, Septoria, Cercospora and Alternaria); Basidiomycetes (e.g. of the genera Hemileia, Rhizocotonia, Puccinia); and, in particular, against the class of the Ascomycetes (e.g. Venturia, Podosphaera, Erysiphe, Monilinia, Uncinula). They can also be used as dressing agents for protecting seeds (fruit, tubers, grains) and plant cuttings against fungus infections.

Accordingly, the invention also relates to pesticidal compositions, especially phytofungicidal compositions, and to the use thereof in agriculture or related fields.

The present invention further embraces the preparation of such compositions which comprises homogeneously mixing the active ingredient with one or more compounds or groups of compounds described herein. The invention furthermore relates to a method of treating plants, which comprises applying thereto the compounds of the formula I or the novel compositions.

Target crops to be protected within the scope of the present invention comprise e.g. the following species of plants: cereals (wheat, barley, rye, oats, rice, sorghum and related crops), beet (sugar beet and fodder beet), pomes, drupes and soft fruit (apples, pears, plums, peaches, almonds, cherries, strawberries, rasberries and blackberries), leguminous plants (beans, lentils, peas, soybeans), oil plants (rape, mustard, poppy, olives, sunflowers, coconuts, castor oil plants, cocoa beans, groundnuts), cucumber plants (marrows, cucumber, melons) fibre plants (cotton, flax, hemp, jute), citrus fruit (oranges, lemons, grapefruit, mandarins), vegetables (spinach, lettuce, asparagus, cabbages, carrots, onions, tomatoes, potatoes, paprika), lauraceae (avocados, cinnamon, camphor), or plants such as maize, tobacco, nuts, coffee, sugar cane, tea, vines, hops, bananas and natural rubber plants, as well as ornamentals (composites).

The compounds of formula I are normally applied in the form of compositions and can be applied to the crop area or plants to be treated, simultaneously or in succession, with further compounds. These compounds can be both fertilisers or micronutrient donors or other preparations that influence plant growth. They can also be selective herbicides, insecticides, fungicides, bactericides, nematicides, mollusicides or mixtures of several of these preparations, if desired, together with further carriers, surfactants or application promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilisers.

A preferred method of applying a compound of the formula I or an agrochemical composition which contains at least one of said compounds, is foliar application. The number of applications and the rate of application depend on the risk of infestation by the corresponding pathogen (type of fungus). The compounds of formula I may also be applied to seeds (coating) by impregnating the seeds either with a liquid formulation containing a compound of the formula I, or coating them with a solid formulation. In special cases, further types of application are also possible, e.g. selective treatment of the plant stems or buds.

The compounds of the formula I are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances. Advantageous rates of application are normally from 50 g to 5 kg of active ingredient (a.i.) per hectare, preferably from 100 g to 2 kg a.i./ha, most preferably from 200 g to 600 g a.i./ha.

The formulations, i.e. the compositions, preparations or mixtures containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils, epoxidised vegetable oils such as epoxidised coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiloate or bentonite; and suitable non-sorbent carriers are materials such as calcite or sand. In addition, a great number of pregranulated materials of inorganic or organic nature can be used, e.g. especially dolomite or pulverised plant residues. Particularly advantageous application promoting adjuvants which are able to reduce substantially the rate of application are also natural (animal or vegetable) or synthetic phospholipids of the series of the cephalins and lecithins, e.g. phosphatidyl ethanolamine, phosphatidyl serine, phosphatidyl choline, sphingomyeline, phosphatidyl inisotol, phosphatidyl glycerol, lysolecithin, plasmalogenes or cardiolipin, which can be obtained e.g. from animal or plant cells. Examples of useful physical forms are phosphatidyl choline mixtures. Examples of synthetic phospholipids are dioctanoylphosphatidyl choline and dipalmitoylphosphatidyl choline.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 8 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpropylene glcyol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethylene ethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in "McCutcheon's Detergents and Emulsifiers Annual", MC Publishing Corp. Ringwood, N.J., 1981; Helmut Stache "Tensid-Taschenbuch" (Handbook of Surfactants), Carl Hanser-Verlag, Munich/Vienna, 1981.

The agrochemical compositions usually contain 0.1 to 99%, preferably 0.1 to 95%, of a compound of the formula I, 99.9 to 1%, preferably 99.8 to 5%, of a solid or liquid adjuvant, and 0 to 25%, preferably 0.1 to 25%, of a surfactant.

Whereas commercial products are preferably formulated as concentrates, the end user will normally employ dilute formulations.

The compositions may also contain further ingredients such as stabilisers, antifoams, viscosity regulators, binders, tackifiers as well as fertilisers or other active ingredients in order to obtain special effects.

Such agrochemical compositions also constitute an object of the present invention.

The invention is illustrated in more detail by the following Examples, without implying any restriction to what is described therein. Parts and percentages are by weight.

1. Preparatory Examples:
Example 1.1: Preparation of

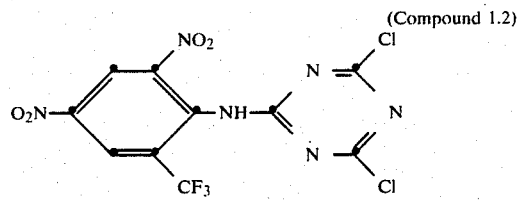

(Compound 1.2)

N-(2'-Trifluoromethyl-4',6'-dinitrophenyl)-2-amino-4,6-dichloropyrimidine

With stirring, 13.2 parts of 85% powdered potassium hydroxide are added, in portions, at room temperature to a solution of 15 parts of 4,6-dichloro-2-aminopyrimidine in 400 ml of tetrahydrofuran. During this addition, the temperature rises to 23° C. in the course of half an hour. The reaction mixture is cooled to 5° C. and 28 parts of 2-chloro-3,5-dinitribenzotrifluoride in 80 ml of tetrahydrofuran are added dropwise in the course of 1 hour to the suspension, which turns red. The reaction mixture is stirred for 15 hours at room temperature, poured into ice-water, acidified with 10 ml of concentrated hydrochloric acid and extracted with two 200 ml portions of ethyl acetate. The combined extracts are washed with two 100 ml portions of water, dried over sodium sulfate, filtered and concentrated by evaporation. The crystalline residue is recrystallised from 400 ml of isopropanol. The yellow crystals so obtained have a melting point of 170°–173° C.

The following compounds of formula I are prepared by procedures analogous to those described above.

TABLE 1

Compounds of the formula

| Comp. | $R_5$ | $R_6$ | $R_7$ | Physical data [°C.] |
|---|---|---|---|---|
| 1.1 | Cl | H | $OCHF_2$ | m.p. 159–161 |
| 1.2 | Cl | H | Cl | m.p. 170–173 |
| 1.3 | $SCH_3$ | CN | H | |
| 1.4 | $OCH_3$ | CN | H | |
| 1.5 | $CH_3$ | $CH_3$ | H | |
| 1.6 | $OCH_3$ | Br | H | |
| 1.7 | $OC_3H_7$—i | H | $OC_3H_7$—i | |
| 1.8 | $CH_3$ | CN | H | |
| 1.9 | $OC_2OC_2H_5$ | H | $CH_3$ | |
| 1.10 | $SC_2H_5$ | H | $CH_3$ | |
| 1.11 | $OC_2H_5$ | H | F | |
| 1.12 | $OCH_3$ | $OC_2H_5$ | H | |
| 1.13 | $CH_3$ | I | $CH_3$ | resin |
| 1.14 | $CH_3$ | CN | $S(O)CH_3$ | |
| 1.15 | $OC_2H_5$ | H | $CH_3$ | |
| 1.16 | $C_4H_9$—i | H | H | |
| 1.17 | Cl | $CH_3$ | H | |
| 1.18 | Cl | H | H | |
| 1.19 | $C_6H_5$ | CN | H | |
| 1.20 | H | $CH_2$—$C_6H_5$ | H | |
| 1.21 | $CH_3$ | CN | $SO_2CH_3$ | |
| 1.22 | $C_3H_7$—n | H | H | |
| 1.23 | Cl | $OCH_3$ | H | |
| 1.24 | $CH_2OCH_3$ | H | $CH_3$ | |
| 1.25 | $CHBr_2$ | Br | H | |
| 1.26 | $OCH_3$ | $OCH_3$ | H | |
| 1.27 | Cl | H | $SC_2H_5$ | semi-crystalline |
| 1.28 | $CH_3$ | $NO_2$ | $SO_2CH_3$ | |
| 1.29 | $SC_3H_7$—i | H | $CH_3$ | |
| 1.30 | Cl | F | H | |
| 1.31 | $OC_2H_5$ | $OCH_3$ | H | |

TABLE 1-continued

Compounds of the formula $$\text{O}_2\text{N}-\text{C}_6\text{H}_2(\text{NO}_2)(\text{CF}_3)-\text{NH}-\text{C}(=\text{N})-\text{C}(R_7)=\text{C}(R_6)-\text{C}(R_5)=\text{N}$$

| Comp. | $R_5$ | $R_6$ | $R_7$ | Physical data [°C.] |
|---|---|---|---|---|
| 1.32 | $CH_3$ | H | $SC_3H_7-n$ | |
| 1.33 | $OCH_3$ | H | H | |
| 1.34 | $CH_3$ | $C_2H_4OC_2H_5$ | H | |
| 1.35 | Cl | H | $SO_2CH_3$ | resin |
| 1.36 | $OC_2H_5$ | $NO_2$ | H | |
| 1.37 | $OCH_3$ | F | H | |
| 1.38 | $CH_3$ | H | $SCH_3$ | |
| 1.39 | $C_4H_9-n$ | H | $CH_3$ | |
| 1.40 | $SC_2H_5$ | H | H | |
| 1.41 | Cl | H | $OC_2H_5$ | resin |
| 1.42 | Cl | $SO_2CH_3$ | H | |
| 1.43 | $C_3H_7-i$ | H | H | |
| 1.44 | H | $C_4H_9-n$ | H | |
| 1.45 | $CH_2OCH_3$ | $OCH_3$ | H | |
| 1.46 | H | CN | H | |
| 1.47 | Cl | $OC_2H_5$ | H | |
| 1.48 | $SO_2C_2H_5$ | H | H | |
| 1.49 | $CH_3$ | H | $O-C_6H_5$ | |
| 1.50 | $OCH_2-C_6H_5$ | H | F | |
| 1.51 | Cl | H | $SCH_3$ | resin |
| 1.52 | F | H | F | |
| 1.53 | Cl | $CH_2-C_6H_5$ | $C_6H_5$ | |
| 1.54 | Br | H | H | |
| 1.55 | Cl | $SCH_3$ | H | |
| 1.56 | $CCl_3$ | H | $CCl_3$ | |
| 1.57 | H | $C_3H_7-i$ | H | |
| 1.58 | $CH_3$ | H | $CF_3$ | |
| 1.59 | Cl | $S-C_6H_5$ | H | |
| 1.60 | $OC_3H_7-i$ | H | $CH_3$ | |
| 1.61 | Cl | H | SCN | semi-crystalline |
| 1.62 | $CH_2-C_6H_5$ | H | $CH_3$ | |
| 1.63 | Cl | $CH_2-C_6H_5$ | Cl | |
| 1.64 | $SCH_2-C_6H_5$ | H | $CH_3$ | |
| 1.65 | Cl | Br | Cl | m.p. 206–208 |
| 1.66 | Cl | $CH_2-C_6H_5$ | $CH_3$ | |
| 1.67 | Cl | H | $OCH_2F$ | resin |
| 1.68 | Cl | $C_6H_5$ | Cl | |
| 1.69 | Cl | Cl | Cl | m.p. 177–178 |
| 1.70 | H | $CH_3$ | H | |
| 1.71 | $SCH_2-C_6H_5$ | H | $SCH_2-C_6H_5$ | |
| 1.72 | Cl | Br | Cl | |
| 1.73 | Cl | $CH_3$ | Cl | |
| 1.74 | H | $OC_4H_9$ | H | |
| 1.75 | Cl | $OC_2H_5$ | Cl | |
| 1.76 | Cl | Cl | $CH_3$ | |
| 1.77 | Cl | $C_5H_9-n$ | $CH_3$ | |
| 1.78 | $SCH_3$ | H | $SCH_3$ | |
| 1.79 | Cl | $C_4H_9-n$ | Cl | |
| 1.80 | H | $OC_4H_9$-sec. | H | |
| 1.81 | H | $NO_2$ | H | |
| 1.82 | $CH_3$ | $C_6H_5$ | $CH_3$ | |
| 1.83 | $CH_3$ | $CH_3$ | $CH_3$ | |
| 1.84 | H | O—cyclohexyl | H | |
| 1.85 | $SC_3H_7-n$ | H | $SC_3H_7-n$ | |
| 1.86 | H | $OC_2H_5$ | H | |
| 1.87 | Br | Cl | Cl | |
| 1.88 | Br | Cl | Br | |
| 1.89 | $OCH_3$ | $OCH_3$ | $OCH_3$ | |
| 1.90 | Cl | H | $OC(CH_3)_2C\equiv CH$ | |
| 1.91 | CN | H | $CH_3$ | |
| 1.92 | Cl | $NO_2$ | $OCH_3$ | |
| 1.93 | H | $OC_2H_4OCH_3$ | H | |
| 1.94 | Cl | H | $C_6H_5$ | |
| 1.95 | $CH_3$ | $CH_2-CH=CH_2$ | $CH_3$ | |
| 1.96 | $C_6H_5$ | H | $C_6H_5$ | |
| 1.97 | $SC_4H_9-n$ | H | $CH_3$ | |
| 1.98 | $CH_3$ | H | $C_6H_5$ | |
| 1.99 | Br | H | Br | |
| 1.100 | $OC_2H_5$ | H | $OC_2H_5$ | |
| 1.101 | H | $CH_2OCH_3$ | H | |

TABLE 1-continued

Compounds of the formula $$O_2N-\text{C}_6H_2(NO_2)(CF_3)-NH-C(=N-)(R_7)...R_6, R_5$$

| Comp. | $R_5$ | $R_6$ | $R_7$ | Physical data [°C.] |
|---|---|---|---|---|
| 1.102 | Cl | $OCH_3$ | Cl | |
| 1.103 | $OCH_3$ | H | $SCH_3$ | |
| 1.104 | Cl | $OCH_3$ | $CH_3$ | |
| 1.105 | Cl | $C_3H_7-n$ | $C_6H_5$ | |
| 1.106 | Cl | $C_6H_3Cl_2(2,4)$ | Cl | |
| 1.107 | Cl | H | $SC_3H_7-n$ | resin |
| 1.108 | Cl | $C_6H_4(CH_3)(4)$ | Cl | |
| 1.109 | Cl | Br | $CH_3$ | |
| 1.110 | Cl | $C_2H_5$ | Cl | |
| 1.111 | Cl | $C_6H_4(OCH_3)(4)$ | Cl | |
| 1.112 | Cl | $CH_3$ | $C_6H_5$ | |
| 1.113 | $C_6H_4(CF_3)(4)$ | CN | H | - |
| 1.114 | Cl | $C_6H_4(NO_2)(4)$ | Cl | |
| 1.115 | Cl | H | $SCH_3$ | resin |
| 1.116 | Cl | H | $OCH_2-phenyl$ | |
| 1.117 | $C_6H_{13}-n$ | H | H | |
| 1.118 | Cl | H | $OCH_2CH=CH_2$ | semi-crystalline |
| 1.119 | Cl | H | $OCH_2C\equiv CH$ | m.p. 130 |
| 1.120 | Cl | Br | $OCH_3$ | |
| 1.121 | Cl | Br | $OC_2H_5$ | |
| 1.122 | Cl | Br | $OC_3H_7-i$ | |
| 1.123 | Cl | Br | $OC_4H_9-sec.$ | |
| 1.124 | Cl | Br | $OCH_2CF_3$ | |
| 1.125 | Cl | Br | $OCH_2CH_2Cl$ | |
| 1.126 | Cl | Br | $OCH_2CH_2Br$ | |
| 1.127 | Cl | Br | $OCHF_2$ | |
| 1.128 | Cl | Br | $OCH_2CH_2OCH_3$ | |
| 1.129 | Cl | Br | $SC_2H_5$ | |
| 1.130 | Cl | Br | $SC_3H_7-i$ | |
| 1.131 | Cl | Br | $OCH_2CH=CH_2$ | m.p. 105-110 |
| 1.132 | Cl | Br | $OC(CH_3)_2C\equiv CH$ | |
| 1.133 | Cl | Br | $OCH_2C\equiv CH$ | m.p. 141-143 |
| 1.134 | Cl | Br | $OCH_2-phenyl$ | |
| 1.135 | Cl | Br | SCN | |
| 1.136 | Cl | Cl | $OCH_3$ | m.p. 168-169 |
| 1.137 | Cl | H | $OCH_3$ | m.p. 169-170 |
| 1.138 | Cl | Cl | $OCH_2CH=CH_2$ | m.p. 115-116 |
| 1.139 | Cl | H | $OCH_2CF_3$ | m.p. 139-140 |
| 1.140 | Cl | Cl | $SC_3H_7-i$ | m.p. 146-148 |
| 1.141 | Cl | Cl | $OCH_2C\equiv CH$ | m.p. 134-135 |
| 1.142 | Cl | Cl | $OCH_2CH_2OCH_3$ | m.p. 102-105 |
| 1.143 | Cl | Cl | $OCH_2CF_3$ | m.p. 138-141 |
| 1.144 | H | $CF_3$ | H | |

TABLE 2

Compounds of the formula $$F_3C-\text{C}_6H_2(NO_2)_2-NH-C(=N-)(R_7)...R_6, R_5$$

| Comp. | $R_5$ | $R_6$ | $R_7$ | Physical data [°C.] |
|---|---|---|---|---|
| 2.1 | Cl | H | Cl | m.p. 144-145 |
| 2.2 | $CH_3$ | Cl | H | |
| 2.3 | $C_6H_{13}-n$ | H | Cl | |
| 2.4 | Br | H | Br | |
| 2.5 | $CH_3$ | Cl | Cl | |
| 2.6 | Cl | $CH_2-C_6H_5$ | Cl | |
| 2.7 | Cl | Br | Cl | m.p. 193-195 |
| 2.8 | Cl | $OC_2H_5$ | Cl | |
| 2.9 | CN | H | $CH_3$ | |
| 2.10 | Cl | $C_4H_9-n$ | Cl | |
| 2.11 | F | H | F | |
| 2.12 | H | CN | H | |

TABLE 2-continued

Compounds of the formula $$F_3C\text{-}C_6H_2(NO_2)_2\text{-}NH\text{-}C(=N\text{-}CR_7)\text{-}N=CR_5\text{-}CR_6$$

| Comp. | $R_5$ | $R_6$ | $R_7$ | Physical data [°C.] |
|---|---|---|---|---|
| 2.13 | $CH_3$ | $CH_3$ | H | |
| 2.14 | Cl | $C_6H_4Cl(4)$ | Cl | |
| 2.15 | $CH_3$ | Br | H | |
| 2.16 | Cl | $C_2H_5$ | Cl | |
| 2.17 | Cl | $C_6H_5$ | Cl | |
| 2.18 | Cl | $C_3H_7-n$ | $C_6H_5$ | |
| 2.19 | Br | $C_6H_5$ | Br | |
| 2.20 | Cl | $CH_3$ | Cl | |
| 2.21 | $CH_3$ | CN | H | |
| 2.22 | Cl | $SCH_3$ | Cl | |
| 2.23 | Cl | $CH_2-C_6H_5$ | H | |
| 2.24 | Br | $C_3H_7-n$ | Br | |
| 2.25 | $SCH_3$ | CN | H | |
| 2.26 | $OCH_3$ | CN | H | |
| 2.27 | $CH_3$ | H | $CH_3$ | m.p. 200–202 |
| 2.28 | Cl | H | $OCH_2CH=CH_2$ | m.p. 124 |
| 2.29 | Cl | H | $OCH_2C\equiv CH$ | m.p. 170–172 |
| 2.30 | Cl | H | $OC(CH_3)_2C\equiv CH$ | |
| 2.31 | Cl | H | $SCH_3$ | m.p. 153 |
| 2.32 | Cl | Cl | $OCH_3$ | m.p. 141–142 |
| 2.33 | Cl | Cl | $OC_2H_5$ | |
| 2.34 | Cl | Cl | $OC_3H_7-i$ | |
| 2.35 | Cl | Cl | $OC_4H_9-\text{sec.}$ | |
| 2.36 | Cl | Cl | $OC(CH_3)_3$ | |
| 2.37 | Cl | Cl | $OCH_2CF_3$ | m.p. 110–111 |
| 2.38 | Cl | Cl | $OCHF_2$ | |
| 2.39 | Cl | Cl | $OCH_2CH_2Cl$ | |
| 2.40 | Cl | Cl | $OCH_2CH_2OC_2H_5$ | |
| 2.41 | Cl | Cl | $OCH_2CH=CH_2$ | m.p. 140–141 |
| 2.42 | Cl | Cl | $OCH_2C\equiv CH$ | m.p. 129–131 |
| 2.43 | Cl | Cl | $OC(CH_3)_2C\equiv CH$ | |
| 2.44 | Cl | Cl | $OCH_2-\text{phenyl}$ | |
| 2.45 | Cl | Cl | SCN | |
| 2.46 | Cl | Cl | $SC_2H_5$ | |
| 2.47 | Cl | Cl | $SC_3H_7-i$ | $n_D^{23}$ 1.6188 |
| 2.48 | Cl | H | $OCH_3$ | m.p. 129–131 |
| 2.49 | Cl | Cl | Cl | m.p. 156–157 |
| 2.50 | Cl | Cl | $OCH_2CH_2OCH_3$ | m.p. 116–117 |
| 2.51 | Cl | Br | $OCH_2CH=CH_2$ | m.p. 120–122 |
| 2.52 | Cl | H | $OCH_2CF_3$ | m.p. 125–126 |
| 2.53 | Cl | Br | $OCH_2C\equiv CH$ | m.p. 143–144 |
| 2.54 | Cl | H | $CH_2Cl$ | m.p. 40–48 |
| 2.55 | Cl | H | $CH_2F$ | m.p. 108–112 |

TABLE 3

Compounds of the formula $$R_2\text{-}C_6H_2(NO_2)(R_1)\text{-}N(R_4)\text{-}C(=N\text{-}CR_7)\text{-}N=CR_5\text{-}CR_6$$

| Comp. | $R_1$ | $R_2$ | $R_4$ | $R_5$ | $R_6$ | $R_7$ | Physical data [°C.] |
|---|---|---|---|---|---|---|---|
| 3.1 | $NO_2$ | $CF_3$ | $C(O)CH_3$ | Cl | H | Cl | m.p. 92–94 |
| 3.2 | $CF_3$ | $NO_2$ | $C(O)CH_3$ | Cl | H | Cl | |
| 3.3 | $NO_2$ | $CF_3$ | $C(O)CH_2Cl$ | Cl | $C_4H_9-n$ | Cl | |
| 3.4 | $NO_2$ | $CF_3$ | $C(O)CH_2OCH_3$ | Cl | $CH_3$ | Cl | |
| 3.5 | $NO_2$ | $CF_3$ | $C(O)CH_3$ | Cl | $OC_2H_5$ | Cl | |
| 3.6 | $CF_3$ | $NO_2$ | $C(O)CH_2OC_2H_5$ | Cl | $CH_3$ | Cl | |
| 3.7 | $CF_3$ | $NO_2$ | $C(O)CH_2OCH_3$ | Cl | CN | $CH_3$ | |
| 3.8 | $NO_2$ | $CF_3$ | $C(O)CH_3$ | $SCH_3$ | CN | H | |
| 3.9 | $NO_2$ | $CF_3$ | $C(O)CH_3$ | $OCH_3$ | CN | H | |

2. Formulation Examples

| 2.1. Emulsifiable concentrates | (a) | (b) | (c) |
|---|---|---|---|
| a compound of the Tables | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | 15% | 20% |
| xylene mixture | 65% | 25% | 20% |

Emulsions of any required concentration can be produced from such concentrates by dilution with water.

| 2.2. Solutions | (a) | (b) | (c) | (d) |
|---|---|---|---|---|
| a compound of the Tables | 80% | 10% | 5% | 95% |
| ethylene glycol monomethyl ether | 20% | — | — | — |
| polyethylene glycol 400 | — | 70% | — | — |
| N—methyl-2-pyrrolidone | — | 20% | — | — |
| epoxidised coconut oil | — | — | 1% | 5% |
| petroleum distillate (boiling range 160-190°) | — | — | 94% | — |

These solutions are suitable for application in the form of microdrops.

| 2.3. Granulates | (a) | (b) |
|---|---|---|
| a compound of the Tables | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 2.4. Dusts | (a) | (b) |
|---|---|---|
| a compound of the Tables | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.
Formulation examples for solid active ingredients of formula I (throughout, percentages are by weight)

| 2.5. Wettable powders | (a) | (b) | (c) |
|---|---|---|---|
| a compound of the Tables | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7-8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| 2.6. Emulsifiable concentrate | |
|---|---|
| a compound of the Tables | 10% |
| octylphenol polyethylene glycol ether (4-5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| 2.7. Dusts | (a) | (b) |
|---|---|---|
| a compound of the Tables | 5% | 8% |
| talcum | 95% | — |
| kaolin | — | 92% |

Ready-for-use dusts are obtained by mixing the active ingredient with the carrier, and grinding the mixture in a suitable mill.

| 2.8. Extruder granulate | |
|---|---|
| a compound of the Tables | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| 2.9. Coated granulate | |
|---|---|
| a compound of the Tables | 3% |
| polyethylene glycol 200 | 3% |
| kaolin | 94% |

The finely ground active ingredient is uniformly applied, in a mixer, to the kaolin moistened with polyethylene glycol. Non-dusty coated granules are obtained in this manner.

| 2.10. Suspension concentrate | |
|---|---|
| a compound of the Tables | 40% |
| ethylene glycol | 10% |
| nonylphenol polyethylene glycol (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the aduvants, giving a suspension concentrate from which suspensions of any desired concentration can be obtained by dilution with water.

3. Biological Examples

Example 3.1: Residual-protective action against Puccinia graminis on wheat

Wheat plants are treated 6 days after sowing with a spray mixture (0.02%) prepared from a wettable powder formulation of the test compound. After 24 hours the treated plants are infected with a uredospore suspension of the fungus. The infected plants are incubated for 48 hours at 95–100% relative humidity and about 20° C. and then stood in a greenhouse at about 22° C. Evaluation of rust pustule development is made 12 days after infection.

Compounds of the Tables have a very good action against Puccinia fungi. Puccinia attack on untreated and infected control plants was 100%. Compounds 1.1, 1.2, 1.137, 1.139, 1.143 and others inhibited Puccinia attack to 0 to 5%.

Example 3.2: Residual protective action against Cercospora arachidicola on groundnut plants Groundnut plants 10–15 cm in height are sprayed with a spray mixture (0.02%) prepared from a wettable powder formulation of the test compound and infected 48 hours later with a conidia suspension of the fungus. The infected plants are incubated for 72 hours at about 21° C. and high humidity and then stood in a greenhouse until the typical leaf specks occur. Evaluation of the fungicidal action is made 12 days after infection and is based on the number and size of the specks.

Compared with untreated and infected controls (number and size of the specks=100%), Cercospora attack on groundnut plants treated with compounds of the Tables is substantially reduced. In the above tests, compounds 1.1, 1.2, 1.69, 1.133, 1.136, 1.141 and 1.143 inhibited the occurrence of specks almost completely (0–10%).

Example 3.3: Residual protective action against Erysiphe graminis on barley

Barley plants about 8 cm in height are sprayed with a spray mixture (0.002%) prepared from a wettable powder formulation of the test compound. The treated plants are dusted with conidia of the fungus after 3–4 hours. The infected barley plants are then stood in a greenhouse at about 22° C. The extent of the infestation is evaluated after 10 days.

Compounds of formula I have a good action against Erysiphe fungi. Erysiphe attack was 100% on untreated and infected control plants. Compounds of Tables 1 and 2 inhibited fungus attack on barley to less than 30%.

Example 3.4: Residual-protective action against Venturia inaequalis on apple shoots Apple cuttings with 10–20 cm long fresh shoots are sprayed with a spray mixture (0.02%) prepared from a wettable powder formulation of the test compound. The plants were infected 24 hours later with a conidia suspension of the fungus. The plants are then incubated for 5 days at 90–100% relative humidity and stood in a greenhouse for a further 10 days at 20°–24° C. Scab infestation is evaluated 15 days after infection. Compounds 1.1, 1.2, 1.69, 1.131, 1.133, 1.139, 1.141, 1.142 and 1.143 inhibited attack to 0–10%. On the other hand, attack on untreated and infected control shoots was 100%.

Example 3.5: Residual protective action against Botrytis cinerea on beans

Bean plants about 10 cm in height are sprayed with a spray mixture (0.02%) prepared from a wettable powder formulation of the test compound. After 48 hours, the treated plants are infected with a conidia suspension of the fungus. The infected plants are incubated for 3 days at 95–100% relative humidity and 21° C., and evaluation of fungus attack is then made. Numerous compounds of Table 1 very strongly inhibit the fungus infection. At a concentration of 0.02%, e.g. compounds 1.1, 1.2, 1.69, 1.131, 1.133, 1.136, 1.138, 1.139 and 1.143 were fully effective (0 to 10% attack). Botrytis attack on untreated and infected bean plants was 100%.

Example 3.6: Residual protective action against Phytophthora infestans on tomato plants After a cultivation period of 3 weeks, tomato plants are sprayed with a spray mixture (0.02%) prepared from a wettable powder formulation of the test compound. After 24 hours the treated plants are infected with a sporangia suspension of the fungus. Evaluation of fungus attack is made is made after the plants have been incubated for 5 days at 95–100% relative humidity and 20° C.

In the above tests, compounds 1.1, 1.2, 1.65, 1.69, 1.119, 1.131, 1.133, 1.136, 1.138, 1.140, 1.141, 1.142 and 1.143 have a very good action. These compounds inhibited fungus attack almost completely (0 to 10% attack) as against 100% attack on untreated control plants.

Example 3.7: Residual protective action against Plasmapora viticola on vines

Vine seedlings in the 4–5 leaf stage are sprayed with a spray mixture (0.02%) prepared from a wettable powder formulation of the test compound. After 24 hours the treated plants are infected with a sporangia suspension of the fungus. Fungus attack is evaluated after incubation for 6 days at 95–100% relative humidity and 20° C.

Compounds of the Tables have a very good fungicidal action against Plasmopara viticola on vines. In particular, compounds 1.1, 1.2, 1.69, 1.131, 1.133, 1.136, 1.138, 1.139, 1.141, 1.142, 1.143, 2.52 and 2.53 inhibited fungus attack complete (0 to 5%).

Example 3.8: Residual protective action against Pyricularia oryzae on rice plants After a cultivation period of 2 weeks, rice plants are sprayed with a spray mixture (0.02%) prepared from a wettable powder formulation of the test compound. After 48 hours the treated plants are infected with a conidia suspension of the fungus. Evaluation of fungus attack is made after incubation for 5 days at 95–100% relative humidity and 24° C.

Compared with 100% attack on untreated controls, fungus attack was less than 10% on rice plants which have been treated with one of compounds 1.143 or 2.54.

What is claimed is:

1. A compound of the formula

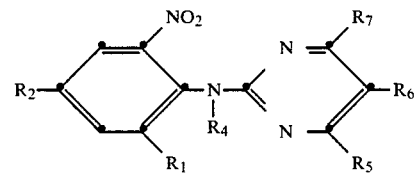

wherein $R_1$ is $CF_3$; $R_2$ is $NO_2$; $R_4$ is H; $R_5$ is Cl; $R_6$ is H, Cl or Br; and $R_7$ is Cl, $OCHF_2$, $OCH_3$, $OCH_2CF_3$, $OCH_2CH{=}CH_2$ or $OCH_2C{\equiv}CH$.

2. A compound according to claim 1, selected from the series consisting of:
N-(2'-trifluoromethyl-4',6'-dinitrophenyl)-2-amino-4-chloro-6-difluoromethoxypyrimidine;
N-(2'-trifluoromethyl-4',6'-dinitrophenyl)-2-amino-4,6-dichloropyrimidine;
N-(2'-trifluoromethyl-4',6'-dinitrophenyl)-2-amino-4,5,6-trichloropyrimidine;
N-(2'-trifluoromethyl-4',6'-dinitrophenyl)-2-amino-4,5-dichloro-6-methoxypyrimidine;
N-(2'-trifluoromethyl-4',6'-dinitrophenyl)-2-amino-4-chloro-5-bromo-6-propin-2-yloxypyrimidine;

N-(2'-trifluoromethyl-4',6'-dinitrophenyl)-2-amino-4-chloro-5-bromo-6-propen-2-yloxypyrimidine;

N-(2'-trifluoromethyl-4',6'-dinitrophenyl)-2-amino-4,5-dichloro-6-(2,2,2-trifluoroethoxypyrimidine.

3. A composition for controlling microorganisms which contains as active ingredient a compound selected from the series of:

N-(2'-trifluoromethyl-4',6'-dinitrophenyl)-2-amino-4-chloro-6-difluoromethoxypyrimidine;

N-(2'-trifluoromethyl-4',6'-dinitrophenyl)-2-amino-4,6-dichloro-pyrimidine;

N-(2'-trifluoromethyl-4',6'-dinitrophenyl)-2-amino-4,5,6-trichloropyrimidine;

N-(2'-trifluoromethyl-4',6'-dinitrophenyl)-2-amino-4,5-dichloro-6-methoxypyrimidine;

N-(2'-trifluoromethyl-4',6'-dinitrophenyl)-2-amino-4-chloro-5-bromo-6-propin-2-yloxypyrimidine;

N-(2'-trifluoromethyl-4',6'-dinitrophenyl)-2-amino-4-chloro-5-bromo-6-propen-2-yloxypyrimidine and N-(2'-trifluoromethyl-4',6'-dinitrophenyl)-2-amino-4,5-dichloro-6-(2,2,2-trifluoroethoxypyrimidine, in combination with conventional adjuvants or surfactants.

* * * * *